(12) United States Patent
Frank et al.

(10) Patent No.: US 7,833,243 B2
(45) Date of Patent: Nov. 16, 2010

(54) MEDICAL GRASPING AND HOLDING INSTRUMENT

(75) Inventors: Timothy Graham Frank, Fife (GB); James Gove, Dundee (GB)

(73) Assignee: Karl Storz GmbH & Co. KG (DE)

( * ) Notice: Subject to any disclaimer, the term of this patent is extended or adjusted under 35 U.S.C. 154(b) by 1424 days.

(21) Appl. No.: 10/849,400

(22) Filed: May 19, 2004

(65) Prior Publication Data
US 2005/0033356 A1 Feb. 10, 2005

Related U.S. Application Data

(63) Continuation of application No. PCT/EP03/05048, filed on May 14, 2003.

(30) Foreign Application Priority Data
Jun. 1, 2002 (DE) ................................ 102 24 500

(51) Int. Cl.
*A61B 17/00* (2006.01)
(52) U.S. Cl. .................... 606/206; 606/208; 81/375; 81/376; 81/377; 81/383
(58) Field of Classification Search .............. 606/205, 606/206, 208, 210; 81/316, 318, 319, 320, 81/321, 324, 367–383
See application file for complete search history.

(56) References Cited

U.S. PATENT DOCUMENTS

| 2,711,663 | A | * | 6/1955 | Petersen | ...................... 81/370 |
| 2,930,376 | A | | 3/1960 | Rathmann | ................... 128/305 |
| 4,192,314 | A | | 3/1980 | Curutchet | ................... 128/322 |
| 4,462,404 | A | * | 7/1984 | Schwarz et al. | ............. 606/206 |
| 5,104,397 | A | | 4/1992 | Vasconcelos et al. | ........ 606/206 |
| 5,233,893 | A | * | 8/1993 | Schmidt | ....................... 81/368 |
| 5,300,082 | A | | 4/1994 | Sharpe et al. | ................ 606/147 |
| 5,797,956 | A | | 8/1998 | Furnish et al. | .............. 606/205 |
| 5,928,263 | A | | 7/1999 | Hoogeboom | ................ 606/205 |
| 5,935,126 | A | | 8/1999 | Riza | ............................ 606/51 |
| 6,227,080 | B1 | * | 5/2001 | Grayo et al. | .................. 81/368 |

FOREIGN PATENT DOCUMENTS

DE  690 24 396 T2  8/1996

\* cited by examiner

*Primary Examiner*—Todd E Manahan
*Assistant Examiner*—Michael G Mendoza
(74) *Attorney, Agent, or Firm*—St. Onge Steward Johnston & Reens LLC

(57) ABSTRACT

The invention relates to a medical grasping and holding instrument with a handle consisting of two handgrips and with a holding portion that consists of at least two jaw members and can be activated by the handle. The jaw members of the holding portion can be locked by means of a spring element both in an end position that releases the holding portion and in an end position that locks the holding portion. In order to create a medical grasping and holding instrument that is of simple construction, can be operated with just one hand, and is easy to clean, it is proposed with this invention that the spring element, configured as a flat spring, for locking the jaw members in their end positions is mounted between the handgrips of the handle so as to connect the two handgrips to one another in such a way that the spring element can be moved by way of a bearing point of a handgrip at the spring element between two end positions that release the spring element.

7 Claims, 4 Drawing Sheets

MEDICAL GRASPING AND HOLDING INSTRUMENT

This application is a continuation of pending International Patent Application No. PCT/EP03/05048 filed May 14, 2003 which designates the United States and claims priority of pending German Application No. 10224500 filed Jun. 1, 2002.

FIELD OF INVENTION

The invention relates to a medical grasping and holding instrument with a handle consisting of two handgrips and with a holding portion that consists of at least two jaw members and can be activated by the handle. The jaw members of the holding portion can be locked in place by means of a spring element both in an end position that releases the holding portion and in an end position that locks the holding portion.

Medical grasping and holding instruments are used for an extremely wide range of purposes, for instance as forceps or needle holders. These known grasping and holding instrument are frequently constructed in pincer shapes and have two lever arms that can swivel around a common rotation axis; the distal ends of the lever arms form the holding portion and the proximal ends form the handle. To move the holding portion into the closed position, it is necessary to press the handgrips of the handle together and to hold them in this position.

The need to keep the handgrips of the handle pressed together in the closed position of the holding portion clearly restricts the surgeon's freedom of movement during an operation. This problem is exacerbated in the HALS (Hand Assisted Laparoscopic Surgery) operating technique, in which, besides inserting the laparoscope and possibly also laparoscopic instruments into the peritoneal cavity, a tissue incision is made to insert one of the operator's hands, so that the operator can use tactile sense, while observing and monitoring through the laparoscope, to perform a more finely controlled operation.

During an operation the surgeon assists the work, with one hand in the patient's peritoneal cavity, by guiding and operating a grasping and holding instrument, such as a needle holder for instance, with this hand that is in the peritoneal cavity. The ability to support the operation, however, is clearly restricted if the hand's freedom of movement is basically limited to holding the handgrips of the handle pressed together to avoid losing a part, such as a needle, that is gripped by the grasping portion.

U.S. Pat. No. 2,930,376 introduces a pincer-type instrument with two handles and a holding portion consisting of two jaw members, where one jaw member is in one piece and rigidly connected with a handle and the other jaw member is pivotally connected with the other handle to swivel around a pivot point. In addition, this known instrument has a spring element, which is configured as a spiral spring and connects the rigid handgrip with the rotatable jaw member, as well as a knee lever that allows the rotatable handgrip to support itself on an adjustable screw mounted on the rigid handgrip.

The knee lever serves at the same time as an abutment bearer for the rotatable handgrip, so that when the rotatable handgrip is pulled toward the rigid handgrip, the jaw member pretensioned in the open position by the spiral spring can be stored into a closed position.

This known surgical instrument includes a few disadvantages in terms of construction, that is, on the one hand, the use of the spiral spring as a spring element, since spiral springs, with their coils held in tension close to one another, are very difficult to clean and, on the other hand, the use of the knee lever. The knee lever constitutes not just an additional individual part that must be produced and installed, but in the known configuration there is also the great risk that the user of the instrument can catch fingers between the knee lever and the handgrip when the handgrip snaps into the closed position.

On the basis of the foregoing, the object of the invention is to create a medical grasping and holding instrument of the aforementioned type, which is simple in construction and can be operated with just one hand and can be cleaned easily.

This object is fulfilled by the invention in a distinctive manner whereby the spring element, configured as a flat spring, connects the two handgrips together and is situated between the handgrips of the handle in such a way that the spring element, to lock the jaw members in their end positions, can be shifted through a bearing point of one handgrip on the spring element between two end positions that relax the spring element.

The invention's particular configuration of the medical instrument makes it possible to guide and activate the instrument safely and simply with one hand, since the handgrips or the jaw members of the holding portion, by means of spring elements configured as flat springs installed between the handgrips, can be moved into their end positions in which the handgrips can be held without exerting extreme pressure. An instrument of this configuration is thus ideally suited as well to the HALS operating technique, in which the operator has only one hand available for managing a medical instrument.

The simple construction, in the simplest case having only three components, that is, two handgrips equipped with one jaw member each and a spring element connecting the handgrips to one another, also ensures cost-effective manufacture and easy cleaning, especially since the spring element is configured as a flat spring that can be easily and thoroughly cleaned.

In a practical embodiment of the invention, it is proposed that the spring element in the opening direction of the handgrips, and thus of the end position that releases the holding portion, is mounted so as to be pretensioned between the handgrips. The pretensioning of the spring element in the opening direction of the handgrips ensures that there is no chance of accidentally activating the holding portion and thus, for instance, inadvertently pinching the patient's tissue.

It is further proposed, according to the invention, that the spring element is mounted with one end in the area of the proximal end of one handgrip and with the other end in the center area of the other handgrip. Because of this distancing of the bearing points of the spring element on the handgrips, the pressure that is required in order to press the handgrips together to close the holding portion is reduced.

Moving the handgrip down to the lower end position, which locks the holding portion, can be facilitated according to the invention if, for storing the spring element in the center area of the handgrip, an extension is formed on this handgrip protruding into the central area between the two handgrips and if the spring element is stored on its free end.

In a first practical embodiment of the invention, one handgrip of the handle is rigidly conjoined, as a single piece, with one jaw member of the holding portion, while the other handgrip of the handle is pivotally connected with the other jaw member of the holding portion so that it can swivel around a pivot point. In this embodiment of the invention it is proposed that the spring element is stored with one end in the area of the proximal end of the rigid handgrip and with the other end in the center area of the rotatable handgrip.

Thanks to this design, it is possible, in simple and reliable manner, for the bearing point, on which the spring element is stored in the center area of the handgrip, to be positioned in the lower end position, which locks the holding portion, below a line which connects the pivot point between the rotatable handgrip and the rotatable jaw member with the bearing point of the spring element in the area of the proximal end of the rigid handgrip. This positioning below this imaginary line means that an external force is required to move the handgrip apart again.

However, in the upper end position that releases the holding portion, the bearing point where the spring element is stored in the center area of the handgrip is situated above a line which connects the pivot point between the rotatable handgrip and the rotatable jaw member with the bearing point of the spring element in the area of the proximal end of the rigid handgrip.

In a second practical embodiment o the invention it is proposed that both handgrips of the handle are configured as a single piece, each rigidly conjoined with one jaw member of the holding portion, and that the handgrips or jaw members are stored so that they can swivel, crossing one another in opposite directions, around a common pivot point. In this pincer-like structure, depending on the position of the bearing point where the spring element is stored in the center area of the one handgrip to the position of the bearing point where the spring element of the other handgrip is stored, the spring element causes the jaw members, aside from an unstable intermediate position, either to be pushed together as far as the closed end position, or to be pushed apart as far as the open end position. The bearing point at which the spring element in the center area of the handgrip is stored is, in this embodiment, arranged on an arc around the pivot point.

With a third practical embodiment of the invention it is proposed that at least one jaw member of the holding portion should be linked firmly with one spring element, and that the spring element, pretensioned between the pivot point on the distal side to swivel at least one jaw member, and a rigid abutment bearer on the proximal side, should be arranged so that each spring element can be moved, by one handgrip of the handle at a time, between the end position that releases the holding portion and the end position that locks the holding portion.

It is advantageous in this third embodiment of the invention that a jaw member of the holding portion is configured as a one-piece unit rigidly conjoined with a handgrip of the handle and that the other jaw member of the holding portion is firmly connected with a spring element, so that the abutment bearer of the spring element is connected rigidly with the rigid handgrip and the other handgrip of the handle is stored so that it can swivel around a pivot point on the proximal end of the rigid handgrip, and that this rotatable handgrip is connected with the spring element.

It is further proposed, with this invention, that the grasping instrument is a needle holder, especially a needle holder for the HALS operating technique. A design according to the invention is especially advantageous for the HALS operating technique because the instrument can be operated easily with a single hand.

Finally, it is proposed with the invention that the grasping and holding instrument is a tube-shaft instrument where the handle is connected with the holding portion by means of at least one power transmission element, in particular a push-pull rod. Through this design, the area of application of the handle designed according to the invention for activating a holding portion is clearly expanded, because the holding portion that can be locked in both end positions is not, in the manner of a pincer, required to be directly connected with the handgrips of the handle.

Additional objects and advantages of the invention will be set forth in the description of the related illustration which follows, in which four embodiments of a medical grasping and holding instrument according to the invention are presented by way of example.

DETAILED DESCRIPTION OF EMBODIMENTS

Figure 1A:
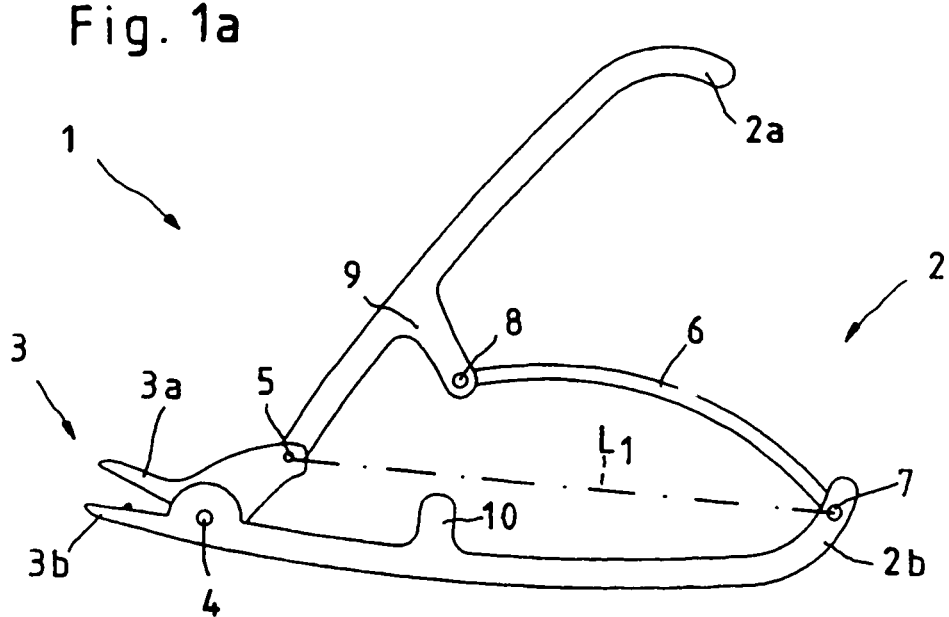
FIG. 1a shows a side view of a first embodiment of a medical instrument according to the invention, with the holding portion in the open end position.

In the medical grasping and holding instruments illustrated in FIGS. 1a to 3c, we see a surgical needle holder 1, in particular for use in laparoscopic surgery according to the HALS operating technique.

The needle holders 1, basically pincer-like in shape, consist essentially of a handle 2 on the proximal side with two handgrips 2a and 2b and with a holding portion 3 on the distal side with two jaw members 3a and 3b, which can swivel on a pivot point 4 relative to one another.

Figure 1B:
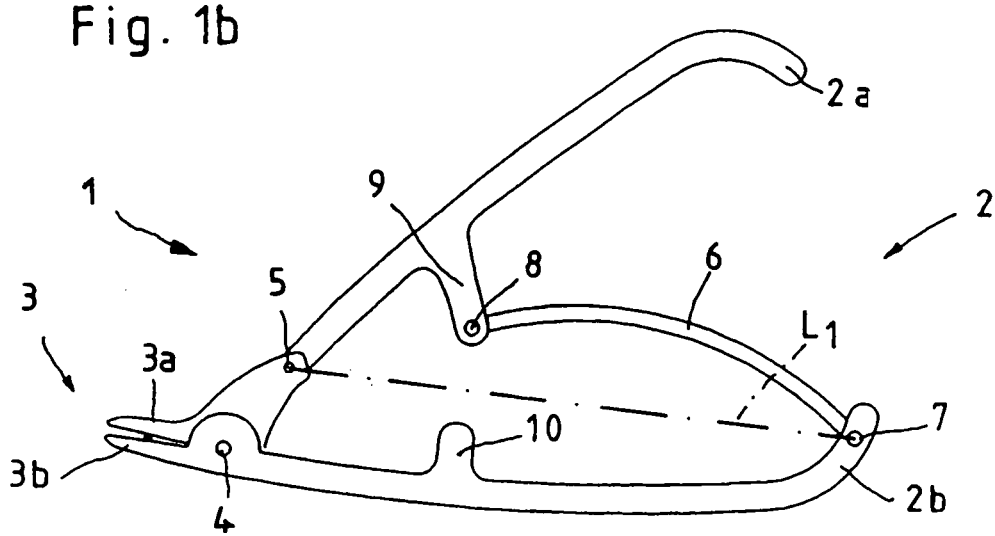
FIG. 1b shows a depiction corresponding to FIG. 1a but with the medical instrument in a holding position.
Figure 1C:
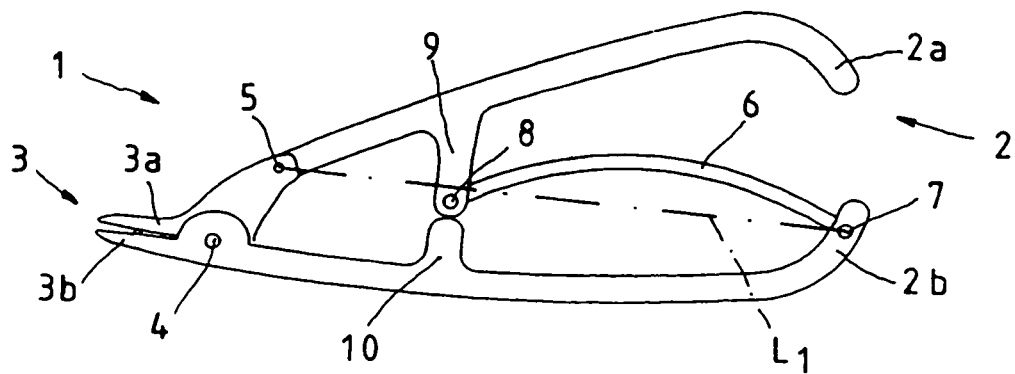
FIG. 1c shows a depiction corresponding to FIGS. 1a and 1b but with the holding portion in the closed end position.

In the first embodiment of the needle holder 1, illustrated in FIGS. 1a to 1c, the handgrip 2b and the jaw member 3b are conjoined to one another as a rigid single unit, whereas the other handgrip 2a and the other jaw member 3a are connected to one another in such a way that they can swivel on a pivot point 5. In this illustrated embodiment, the jaw members 3a, 3b or the handgrips 2a, 2b do not intersect with one another.

As can further be seen from the illustrations of FIGS. 1a to 1c, a spring element 6 configured as a flat spring is situated between the handgrips 2a and 2b of the handle 2 and is stored with one end on a bearing point 7 in the area of the proximal end of the rigid handgrip 2b and with the other end on a bearing point 8 in the center area of the rotatable handgrip 2a. The spring element 6 is stored in the center area of the rotatable handgrip 2a, in the illustrated embodiment of the needle holder 1, on the free end of an extension 9 that is installed on the rotatable handgrip 2a and protrudes into the space between the two handgrips 2a, 2b.

This medical grasping and holding instrument illustrated in FIGS. 1a to 1c is operated as follows:

In the HALS operating technique, the surgeon, holding and protecting the needle holder 1 in the palm of the hand, inserts it along with his/her hand through a suitable skin opening into the patient's peritoneal cavity, while the needle holder 1 is as much as possible in the position shown in FIG. 1c since this has the most compact structure.

In the open end position of the holding portion 3 illustrated in FIG. 1a, the handgrips 2a and 2b are pressed apart by means of the spring element 6 that has been pretensioned in the opening direction of the handgrips 2a, 2b. This position, in which the bearing point 8, where the spring element 6 is stored in the center area of the handgrip 2a, is situated above a line L1 which connects the pivot point 5 between the rotatable handgrip 2a and the rotatable jaw member 3a with the bearing point 7 of the spring element 6 in the area of the proximal end of the rigid handgrip 2b, constitutes an end position of the handgrips 2a, 2b of the handle 2 or of the jaw members 3a, 3b of the holding portion 3, in which end position the spring element 6 locks the handgrips 2a, 2b or the jaw members 3a, 3b, since the handgrips 2a, 2b can be moved out of this end position only by exerting an external force working against the spring force of the spring element 6.

Thus, in order to grasp a needle, the surgeon presses the handgrips 2a, 2b toward one another against the force of the spring element 6 until the needle holder 1 assumes the position illustrated in FIG. 1b, in which the jaw members 3a, 3b of the holding portion 3 are closed holding the needle. In this position the bearing point 8 is found on or somewhat above the line L1, which connects the pivot point 5 with the bearing point 7.

Additional pressing together of the handgrips 2a, 2b causes the spring element 6 to be further bent until the bearing point 8 crosses the line L1, which connects the pivot point 5 with the bearing point 7, since the connection between the handgrip 2a and jaw member 3a buckles toward the pivot point 5 and assumes the second end position depicted in FIG. 1c, in which the handgrips 2a, 2b are pressed together and the jaw members 3a, 3b of the holding portion 3 are closed. Because the spring element 6 is relaxed slightly once again on crossing the line L1, the handgrips 2a, 2b are again locked in this end position, since it requires the exertion of an external force to press the handgrips 2a, 2b apart again against the spring force of the spring element 6.

The movement of the handgrips 2a, 2b toward one another is restricted by a stop 10, which is configured on the rigid handgrip 2b; the extension 9, which is mounted on the rotatable handgrip 2a, runs up against this stop 10.

To open the handgrips 2a, 2b or the jaw members 3a, 3b, the surgeon inserts one or more fingers between the handgrips 2a, 2b and presses the handgrips 2a, 2b apart again against the spring force of the spring element 6.

Because the needle holder 1 is locked in the closed position of the holding portion 3, the surgeon can loosen the grip around the handgrips 2a, 2b of the handle 2 without any risk that the needle grasped by the jaw members 3a, 3b will slip or even fall out of the holding portion 3.

A medical grasping and holding instrument configured in this way is thus ideally suited, especially for the HALS operating technique, since it can be operated simply and safely with just one hand and is held locked by the spring element 6 in its end positions.

Figure 2A:
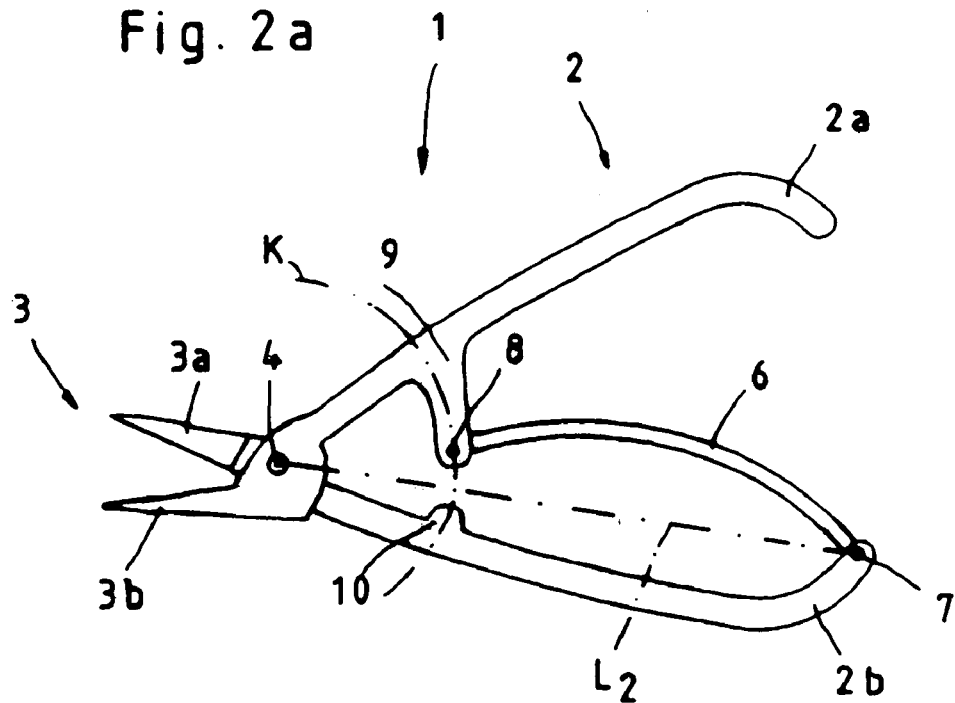
FIG. 2a shows a side view of a second embodiment of a medical instrument according to the invention, with the holding portion in the open end position.
Figure 2B:
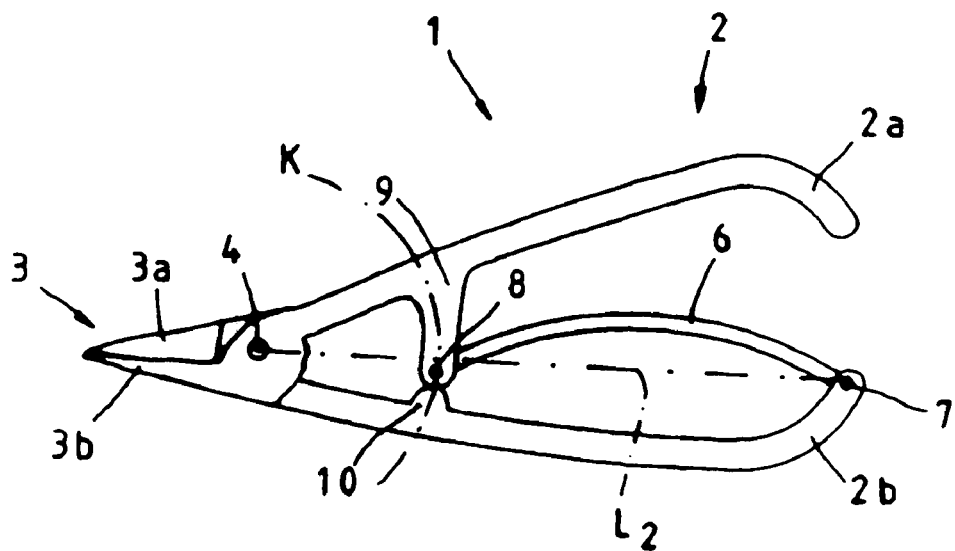
FIG. 2b shows a depiction corresponding to FIG. 2a but with the holding portion in the closed end position.

The second embodiment of the needle holder 1 illustrated in FIGS. 2a and 2b is distinguished from the first embodiment, previously described by means of FIGS. 1a to 1c in that both handgrips 2a, 2b of the handle 2 are rigidly connected with the respective jaw members 3a, 3b of the holding portion 3. In this pincer-like configuration of the needle holder 1, the jaw members 3a, 3b or handgrips 2a, 2b cross one another in the pivot point 4, around which the jaw members 3a, 3b or handgrips 2a, 2b can swivel with respect to one another.

Also in this second embodiment of the needle holder 1, as can be seen from FIGS. 2a and 2b, a spring element 6 configured as a flat spring is situated between the handgrips 2a and 2b of the handle 2, and this spring element 6 is stored with one end in a bearing point 7 in the area of the proximal end of the one handgrip 2b and with the other end at a bearing point 8 in the center area of the other handgrip 2a. The bearing of the spring element 6 in the center area of the rotatable handgrip 2a, also in this illustrated second embodiment of the needle holder 1, takes place at the free end of an extension 9 situated on the handgrip 2a and protruding into the space between the two handgrips 2a, 2b.

This needle holder 1 is operated basically in the same manner as was described before in connection with the first embodiment according to FIGS. 1a to 1c.

However, the spring element 6 is locked in its two end positions, in the second embodiment, by mounting the bearing point 8, where the spring element 6 is stored in the center area of the handgrip 2a, on an arc K around the pivot point 4.

Upon pressing together the handgrips 2a, 2b, starting from the open end position as seen in FIG. 2a, all the way to the closed end position according to FIG. 2b, the spring element 6 is bent further against its spring force, because the distance between the bearing points 8 and 7 is at first reduced until the arc K cuts a line L2, which cuts the pivot point 4 with the bearing point 7 of the spring element 6 in the area of the proximal end of the handgrip 2b. As soon as the handgrips 2a, 2b are further pressed together, the spring element 6 is relaxed again because the distance between the bearing points 7 and 8 is larger again. Because the spring element 6 is loosened again in crossing the line L2, the handgrips 2a, 2b are again stopped in this end position, since it requires the exertion of an external force to press the handgrips 2a, 2b apart again against the spring force of the spring element 6.

Figure 3A:
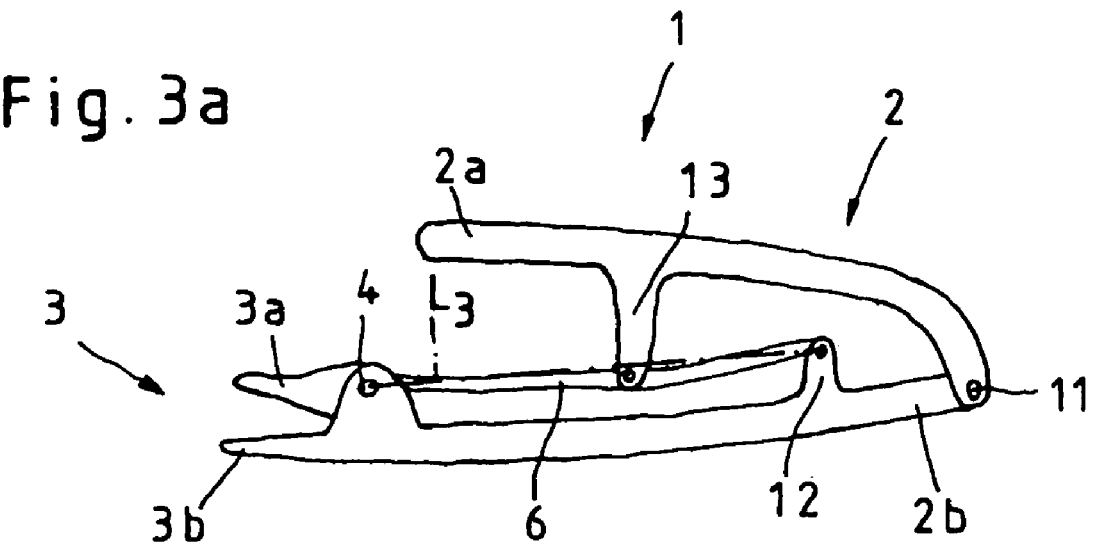
FIG. 3a shows a side view of a third embodiment of a medical instrument according to the invention, with the holding portion in the open end position.

The illustrations in FIGS. 3a and 3c show a third embodiment of the needle holder 1. In this embodiment the needle holder 1, contrary to the embodiments depicted in FIGS. 1a to 2b, has a clearly distinct structure. Whereas in the first and second embodiments the jaw members 3a and 3b are directly connected with the handgrips 2a and 2b respectively, in the third embodiment illustrated in FIGS. 3a and 3b the handgrip 2a is only indirectly connected with the jaw member 3a—that is, it is connected by way of the spring element 6.

Figure 3B:
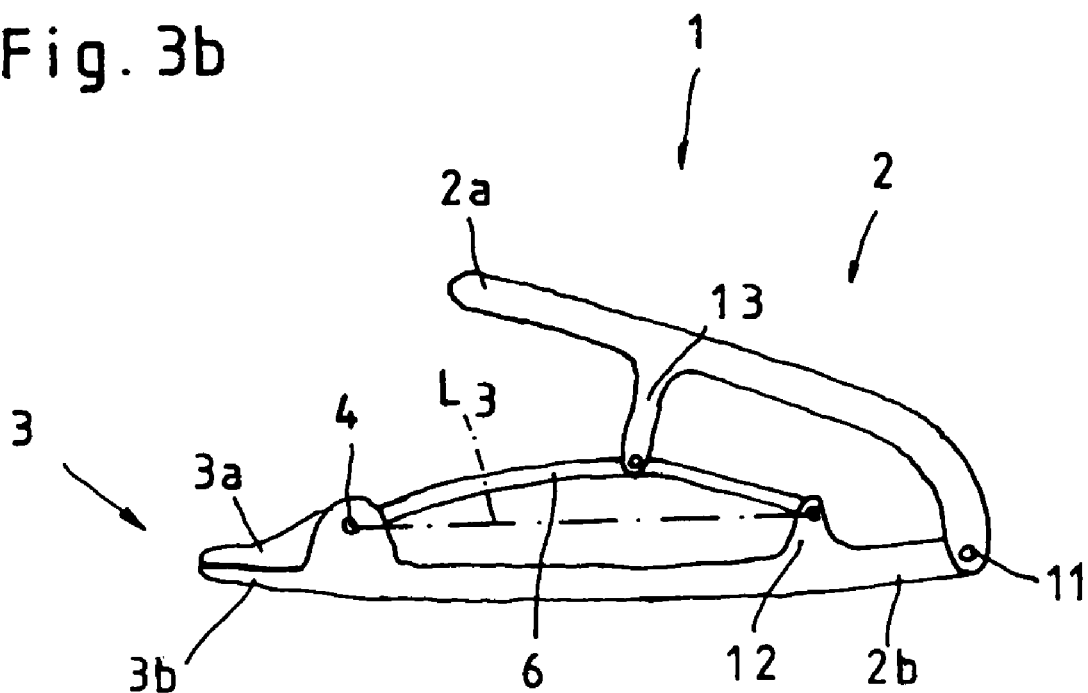
FIG. 3b shows a depiction corresponding to FIG. 3a but with the holding portion in the closed end position.

As can be seen from FIGS. 3a and 3b, the handgrip 2b and jaw member 3b are rigidly conjoined to form one unit. The other handgrip 2a is pivotally stored on the proximal end of the rigid handgrip 3b to swivel around a pivot point 11. The connection between the second jaw member 3a and the handgrip 2a is provided by the spring element 6, which is firmly connected with the jaw member 3a. The spring element 6, pretensioned, is mounted on the distal side between the pivot point 4 to rotate at least the two jaw members 3a, 3b and a rigid abutment bearer 12 on the proximal side arranged on the rigid handgrip 2b in such a way that the spring element 6 can be moved by the handgrip 2a of the handle 2 between an end position that releases the holding portion 3 according to FIG. 3a and an end position that locks the holding portion 3 according to FIG. 3b. The spring element 6 is moved by the handgrip 2a by means of a connecting pin 13 between the handgrip 2a and the spring element 6.

In the open end position depicted in FIG. 3a, the spring element 6 is pushed downward by the handgrip 2a, causing the holding portion 3 to open. Pressing the spring element 6 below a line L3, which connects the two clamping points of the spring element 6 at the pivot point 4 and at the abutment bearer 12 to one another, causes the handgrips 2a, 2b to be locked in this end position because it requires exertion of an external force to pull the handgrips 2a, 2b apart again against the spring force of the spring element 6.

To move the holding portion 3 into the closed end position seen in FIG. 3b, the handgrip 2a must be raised against the spring force of the spring element 6 until the spring element 6, passing over the line L3, bends upward.

Alternatively to this illustrated third embodiment, it is also possible to configure this arrangement of the spring element 6 so that both jaw members 3a, 3b are firmly connected with one spring element 6 each and can be activated only indirectly by way of the handgrips 2a, 2b acting on the spring element 6. In this embodiment, not illustrated, it requires a rigid center pin, on whose distal end the jaw members 3a, 3b can swivel around the pivot point 4 and on whose proximal end the handgrips 2a, 2b are stored so as to be able to swivel around the pivot point 11. In addition, the rigid center pin serves to receive the two abutment bearers 12 for the two spring elements 6.

Figure 4:
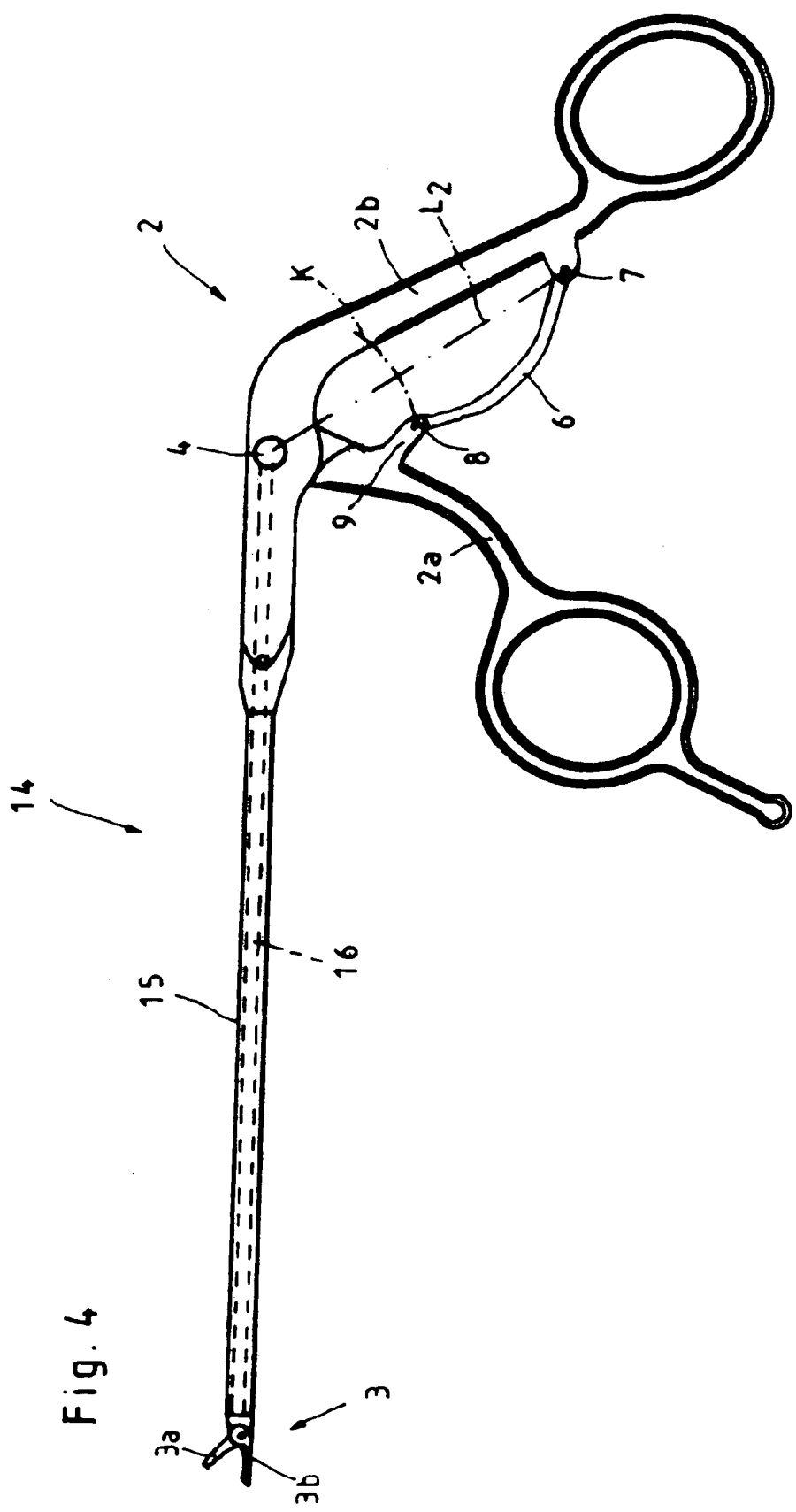
FIG. 4 shows a schematic side view of a fourth embodiment of a medical instrument according to the invention.

FIG. 4, finally, shows a fourth embodiment for configuring a medical grasping and holding instrument. In this illustrated medical instrument we see a tube shaft instrument 14 with a preferably hollow cylindrical shaft 15, on whose proximal end the handle 2 is mounted, consisting of handgrips 2a and 2b, and on whose distal end the holding portion 3, consisting of the two jaw members 3a and 3b, is mounted. To activate the holding portion 3 by means of the handle 2, the handle 2 and the holding portion 3 are connected to one another by means of at least one force transmission element. In the illustrated embodiment, the force transmission element takes the form of a push-pull rod 16.

It is also possible, as an alternative, to configure the force transmission element as a Bowden cable, for instance.

The handles 2 for activating the holding portion 3, in the configuration of the grasping and holding instrument, can be configured in such a way as was previously described in connection with FIGS. 1a to 3b. In all cases, the configuration of at least one spring element 6 allows the holding portion 3 to be locked both in an open end position and in a closed end position.

ILLUSTRATION NUMBER KEY

1 Needle holder
2 Handle
2a (Rotatable) Handgrip
2b (Rigid) Handgrip
3 Holding portion L1 Line
3a (Rotatable) Jaw member L2 Line
3b (Rigid) Jaw member L3 Line
4 Pivot point K Arc
5 Pivot point
6 Spring element
7 Storage point
8 Storage point
9 Extension
10 Stop
11 Pivot point
12 Abutment bearing
13 Connecting pin
14 Tube shaft instrument
15 Shaft
16 Push-pull rod

What is claimed is:

1. A medical grasping and holding instrument with a handle consisting of two handgrips and a holding portion that consists of at least two jaw members and can be actuated by the handle, where the jaw members of the holding portion can be locked by means of a spring element both in an end position with opened jaw members that releases the holding portion and in an end position with closed jaw members that locks the holding portion, wherein the spring element configured as a flat spring and connecting the two handgrips to one another is mounted between the handgrips and fixedly connected to the handgrips of the handle via at least two stationary bearing points in such a way that to lock the jaw members in their end positions, the spring element can be moved by way of a bearing point of one handgrip on the spring element between two end positions that relax the spring element wherein the locking of the two jaw members in both end positions is caused by the spring element only, wherein the handgrip of the handle is configured as to be rigidly conjoined in one piece with one jaw member of the holding portion, while the other handgrip of the handle is pivotally connected with the other jaw member of the holding portion to swivel around a pivot point and wherein the bearing point, where a spring element in the center area of the handgrip is stored, is arranged in a lower end position that locks the holding portion, below a line (L1) which connects the pivot point between a rotatable handgrip and a rotatable jaw member with the bearing point of the spring element in the area of a proximal end of the rigid handgrip.

2. A medical grasping and holding instrument as in claim 1, wherein the spring element is mounted so that it is pretensioned between the handgrips in an opening direction of the handgrips and thus of the end position releasing the holding portion.

3. A medical grasping and holding instrument as in claim 1, wherein the spring element is stored with one end at a bearing point in the area of an proximal end of a handgrip and with the other end at a bearing point in a center area of the other handgrip.

4. A medical grasping and holding instrument as in claim 3, wherein, in order to store the spring element in a center area of the handgrip, on this handgrip an extension is configured protruding into an interval between the two handgrips, on a free end of which extension the spring element is stored.

5. A medical grasping and holding instrument as in claim 1, wherein the spring element is stored with one end at the bearing point in the area of a proximal end of the rigid handgrip and with the other end at the bearing point in a center area of the rotatable handgrip.

6. A medical grasping and holding instrument as in claim 1, wherein the bearing point where the spring element in a center area of the handgrip is stored, is arranged in an upper end position that releases the holding portion, above a line (L1) which connects the pivot point between a rotatable handgrip and a rotatable jaw member with the bearing point of the spring element in the area of a proximal end of the rigid handgrip.

7. A medical grasping and holding instrument as in claim 1, wherein the grasping and holding instrument is a needle holder.

* * * * *